United States Patent
Ishihara et al.

[11] Patent Number: 5,916,161
[45] Date of Patent: Jun. 29, 1999

[54] MAGNETIC RESONANCE IMAGING APPARATUS WITH TEMPERATURE MEASUREMENT FUNCTION

[75] Inventors: Yasutoshi Ishihara; Kazuya Okamoto, both of Tokyo, Japan

[73] Assignee: Kabushiki Kaisha Toshiba, Kawasaki, Japan

[21] Appl. No.: 08/713,430

[22] Filed: Sep. 13, 1996

[30] Foreign Application Priority Data

Sep. 13, 1995 [JP] Japan .................................... 7-235760
Aug. 5, 1996 [JP] Japan .................................... 8-206209

[51] Int. Cl.⁶ .................................................. A61B 05/55
[52] U.S. Cl. .......................... 600/410; 600/412; 324/315
[58] Field of Search ............................. 128/653.1, 653.2, 128/736; 324/309, 315; 600/410, 412, 407, 549

[56] References Cited

U.S. PATENT DOCUMENTS 4,558,279  12/1985  Ackerman et al. ...................... 324/315
5,378,987  1/1995   Ishihara et al. ......................... 324/315
5,553,618  9/1996   Suzuki et al. .

FOREIGN PATENT DOCUMENTS 59-196431  11/1984  Japan .

*Primary Examiner*—George Manuel
*Assistant Examiner*—Shawna J. Shaw
*Attorney, Agent, or Firm*—Foley & Lardner

[57] ABSTRACT

A magnetic resonance imaging apparatus capable of measuring a temperature increase due to an application of RF magnetic fields for data acquisition purpose, and notifying an information on the measured temperature increase regularly to an operator, so as to secure the safety of a body to be examined. In this magnetic resonance imaging apparatus, the image data acquisition operation is controlled to acquire a phase information associated with a temperature change in an interior of the body to be examined, by displacing either an observation start timing or a radio frequency magnetic field application timing for a prescribed magnetic resonance signal in the magnetic resonance signal sequence from a normal timing for acquiring image data.

30 Claims, 14 Drawing Sheets

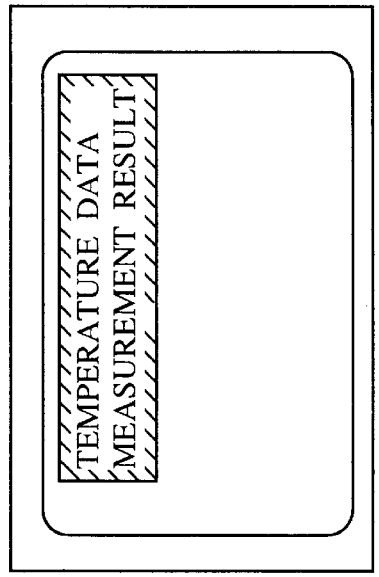

TIME CHANGE

FIG.14A
LIMIT = xxxx
t = xxxx  8888
t = xxxx  8888
t = xxxx  8888
⋮    ⋮
FIG.14B
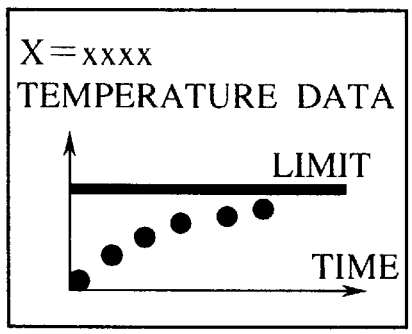
FIG.14E
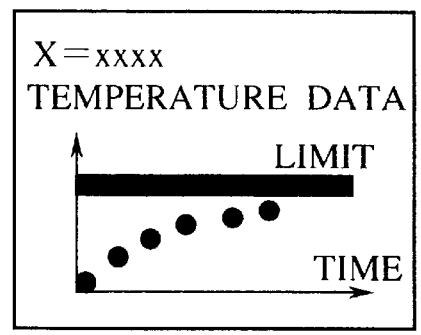
FIG.14C
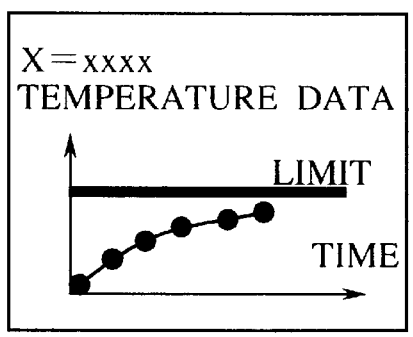
FIG.14F
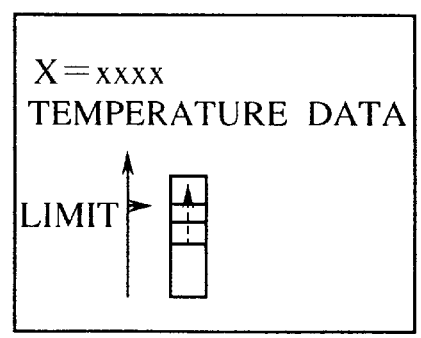
FIG.14D
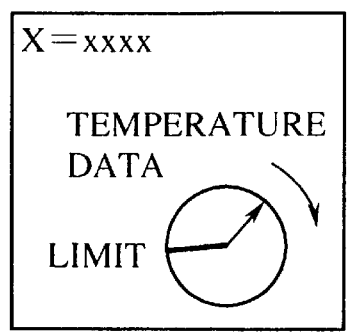

MAGNETIC RESONANCE IMAGING APPARATUS WITH TEMPERATURE MEASUREMENT FUNCTION

BACKGROUND OF THE INVENTION

1. Field of the Invention

The present invention relates to a magnetic resonance imaging (MRI) apparatus for obtaining tomographic images, metabolite distribution, or metabolite images of an interior of a body to be examined by utilizing a nuclear magnetic resonance (NMR) phenomenon, incorporating a function for measuring a temperature increase due to an application of radio frequency magnetic fields.

2. Description of the Background Art

In order to shorten the image data acquisition time in the MRI, an imaging method for applying a plurality of radio frequency (RF) magnetic fields onto a body to be examined within a short period of time is often employed. However, when many RF magnetic fields are applied according to this imaging method, a temperature inside a living body increases due to the induced heating phenomenon.

For this reason, the Food and Drug Administration (FDA) of U.S.A. proposed the first safety standard for the MRI apparatus in 1982 in order to secure the safety of the MRI apparatus with respect to living bodies. This proposal recommends to limit an application of RF power onto a living body according to the specific absorption ratio (SAR). According to the guideline at that time, It was recommended to keep the SAR below 0.4 W/kg for a whole body on average, and below 0.2 W/kg per 1 g of any body part locally. This standard was revised in 1988 to recommend the SAR below 0.4 W/kg for a whole body on average, below 8 W/kg for 1 g of tissue, and 3.2 W/kg for the head. At the same time, it was additionally proposed to keep the body temperature increase below 1° C. at the body center portion, and the temperature below 38° C. at the head, below 39° C. at the trunk portion, and below 40° C. at the hand and leg portions.

However, after the RF power is determined according to the SAR prior to the pulse sequence execution, the pulse sequence is executed regardless of a beat generation state of a body to be examined so that it has been impossible to confirm the safety of a body to be examined.

In addition, the temperature increase in an interior of a body to be examined varies considerably depending on an observed body portion, an observed tissue, and a blood flow state, so that it is impossible to comprehend an actual state of the temperature increase in an interior of a living body from a standard value of the SAR alone. For this reason, even when the pulse sequence is executed by using the applied RF magnetic field power determined in accordance with the SAR standard, there has been a possibility for causing a damage to a body to be examined due to an unexpected temperature increase induced in a body to be examined.

On the contrary, there is also a possibility for overestimating an amount of heat generation, and there have been cases in which the data acquisition cannot be carried out efficiently because the sufficient RF magnetic field power cannot be applied despite of the fact that an excessive heat generation is not likely to occur.

SUMMARY OF THE INVENTION

It is therefore an object of the present invention to provide a magnetic resonance imaging apparatus capable of measuring a temperature Increase due to an application of RF magnetic fields for data acquisition purpose, and notifying an information on the measured temperature increase regularly to an operator, so as to secure the safety of a body to be examined.

It is another object of the present invention to provide a guideline for designing an applicable RF magnetic field power in order to construct an executable pulse sequence.

According to one aspect of the present invention there is provided a magnetic resonance imaging apparatus, comprising: imaging means for observing a magnetic resonance signal sequence by applying a slicing gradient magnetic field in a prescribed direction to a body to be examined placed in a static magnetic field, while applying radio frequency mangnetic fields including a radio frequency selective excitation pulse and a plurality of radio frequency inversion pulses in prescribed intervals to the body to be examined according to a prescribed pulse sequence; and control means for controlling the imaging means to acquire a phase information associated with a temperature change in an interior of the body to be examined, by adjusting a timing in the pulse sequence for a prescribed magnetic resonance signal in the magnetic resonance signal sequence from a normal timing for acquiring image data.

According to another aspect of the present invention there is provided a method of magnetic resonance imaging. comprising the steps of: observing a magnetic resonance signal sequence by applying a slicing gradient magnetic field in a prescribed direction to a body to be examined placed in a static magnetic field, while applying radio frequency mangnetic fields including a radio frequency selective excitation pulse and a plurality of radio frequency inversion pulses in prescribed intervals to the body to be examined according to a prescribed pulse sequence; and controlling the imaging step to acquire a phase information associated with a temperature change in an interior of the body to be examined, by adjusting a timing in the pulse sequence for a prescribed magnetic resonance signal in the magnetic resonance signal sequence from a normal timing for acquiring image data.

Other features and advantages of the present invention will become apparent from the following description taken in conjunction with the accompanying drawings.

BRIEF DESCRIPTION OF THE DRAWINGS

FIGS. 10A to 10F are illustrations of some exemplary temperature data display formats that can be used in the magnetic resonance imaging apparatus of FIG. 1.

FIGS. 14A to 14F are illustrations of some other exemplary temperature data display formats that can be used in the magnetic resonance imaging apparatus of FIG. 1.

DETAILED DESCRIPTION OF THE PREFERRED EMBODIMENTS

Now, the preferred embodiment of a magnetic resonance imaging apparatus according to the present invention will be described with references to the drawings.

Figure 1:
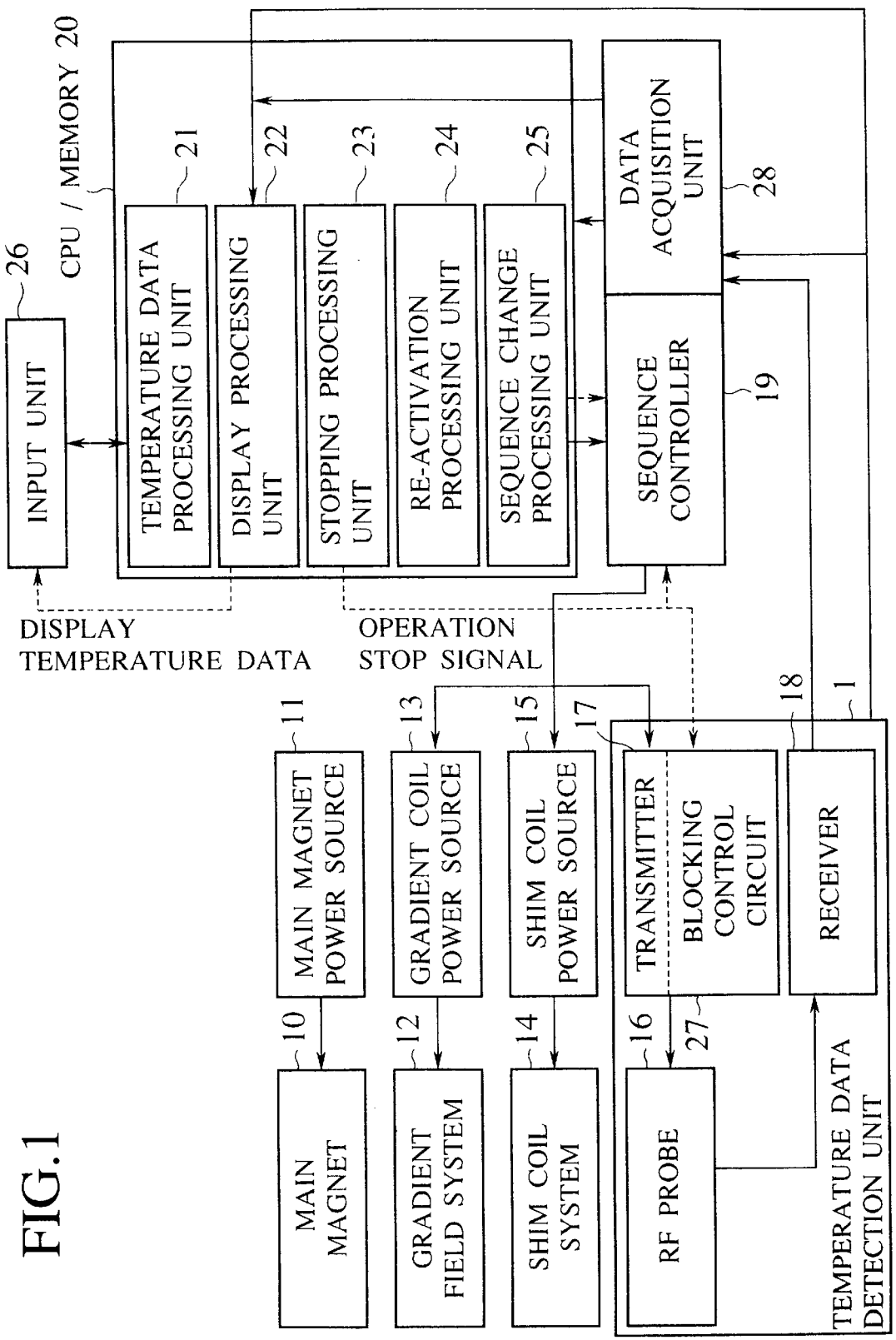
FIG. 1 is a block diagram of one embodiment of a magnetic resonance imaging apparatus according to the present invention.

FIG. 1 shows a magnetic resonance imaging apparatus in one embodiment of the present Invention, for securing the safety of a body to be examined on an account of a temperature increase inside a living body due to an application of RF magnetic fields.

This magnetic resonance imaging apparatus comprises: a main magnet 10 and a main magnet power source 11 for generating a main magnetic field (static magnetic field); gradient field system 12 and gradient coil power source 13 for generating gradient magnetic fields having a linear gradient magnetic field distribution In each one of three orthogonal axial directions X, Y, and Z; a shim coil system 14 including a plurality of shim coils and a shim coil power source 15; an RF probe 16 for applying RF magnetic fields and detecting magnetic resonance (MR) signals (which may be adjusted to detect magnetic resonance signals from more than one types of nuclei), a transmitter (RF transmission amp) 17 for supplying RF signals to the RF probe 16: a receiver 18 for receiving, detecting, and amplifying the MR signals detected by the RF probe 16; a sequence controller 19 and a CPU/memory 20 for controlling a pulse sequence; an input unit 26 connected to the CPU/memory 20; a blocking control circuit 27 attached to the transmitter 17; a data acquisition unit 28 connected between the receiver 18 and the CPU/memory 20; and a temperature data detection unit 1.

In this configuration of FIG. 1, the temperature data detection unit 1 is formed by a thermocouple, for example, and provided in a vicinity of the RF probe 16, the transmitter 17, the receiver 18, and the blocking control circuit 27.

The CPU/memory 20 further includes a temperature data processing unit 21, a display processing unit 22, a stopping processing unit 23, a re-activation processing unit 24, and a sequence change processing unit 25.

The temperature data obtained by the temperature data detection unit 1 is entered into the CPU/memory 20, while the MR signals related to the temperature data are entered Into the CPU/memory 20 through the data acquisition unit 28, and after necessary calculation processing is applied, the processing result is displayed at an output device such as that provided at the input unit 26 connected with the display processing unit 22.

Also, the calculation processing such as a comparison with a preset tolerable value is carried out by the CPU/memory 20, and the execution of the pulse sequence is interrupted by sending a sequence controller stop signal to the sequence controller 19. In addition, an output control signal is sent to a controller of the transmitter 17, and the RF power output is blocked or suppressed by an operation of the blocking control circuit 27.

Figure 2:
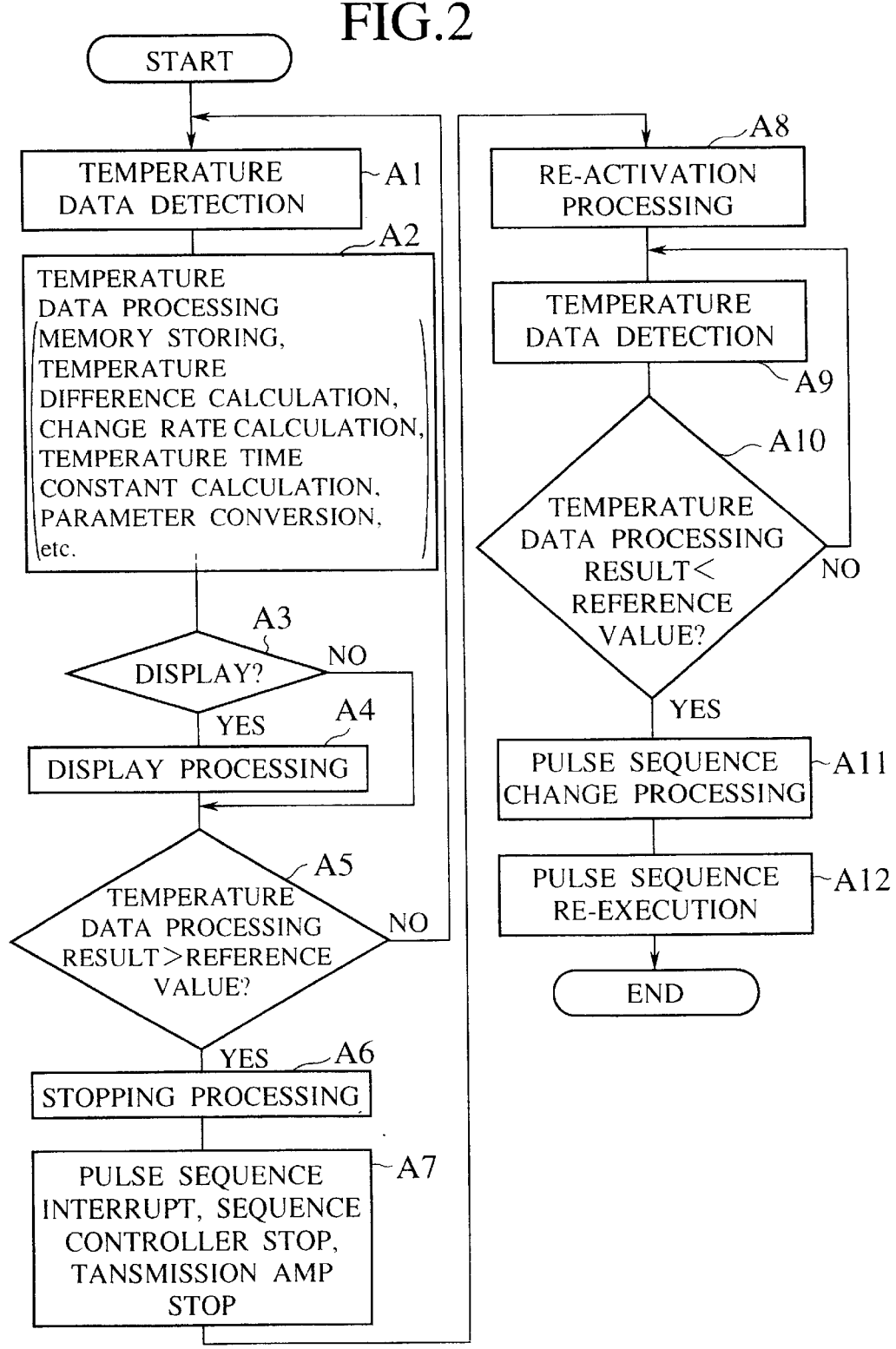
FIG. 2 is a flow chart for the overall operation of the magnetic resonance imaging apparatus of FIG. 1.

Now, with reference to FIG. 2, an outline of the operation by this magnetic resonance imaging apparatus of FIG. 1 will be described.

First, at the temperature data detection unit 1. the detection of temperature data from a body to be examined is carried out (step A1). Then, at the CPU/memory 20, the temperature data processing based on the detected temperature data is carried out (step A2). This temperature processing includes several processing contents as described below, including an information storing into a memory, a calculation of a temperature difference, a calculation of a temperature change rate, a calculation of a temperature time constant, a parameter conversion, etc.

Then, whether or not to display the temperature data measurement result to which the temperature data processing is applied is Judged (step A3). In a case of not displaying, the operation proceeds to the step A5, whereas in a case of displaying, the display processing based on a prescribed format is carried out (step A4).

Next, whether the temperature data processing result obtained at the CPU/memory 20 has reached to a reference value or not is judged (step A5). When the temperature data processing result is not reaching to the reference value. it is judged satisfactory and the operation returns to the step A1 to repeat the same operation. On the other hand, when the temperature data processing result is reaching to the reference value, the stopping processing takes place immediately (step A6), and various processings such as an interruption of the pulse sequence, a stopping of the sequence controller 19, and a stopping of the transmission amp 17 are carried out (step A7).

Afterwards, the re-activation processing is carried out (step A8), and at a time of re-activation, the temperature data detection is carried out again similarly as in the above (step A9). and whether the temperature data processing result has reached to the reference value or not is judged again (step S10). When the temperature data processing result is not reaching to the reference value, the operation returns to the step A9 again to carry out the temperature data detection, whereas when the temperature data processing result is reaching to the reference value, the pulse sequence change processing is carried out (step A11), and the changed pulse sequence is re-executed (step S12).

In the following, each processing in the flow chart of FIG. 2 and corresponding functions of the elements in the configuration of FIG. 1 will be described in detail.

First, the temperature measurement processing scheme will be described, The temperature in a vicinity or on a surface of a body to be examined can be measured in high precision and in real time by a method using a temperature probe such as a thermocouple or an optical fiber thermometer. However, such a method requires a plurality of temperature probes in order to obtain spatial temperature data, so that it cannot be considered as a practical method.

On the other hand, the thermography utilizing infrared rays is a non-invasive method which can obtain two dimensional temperature distribution, but the temperature data of an interior of a living body that can be detected from an external is said to cover only about 2 to 3 mm from a body surface, so that it is difficult to comprehend the temperature increase at a deeper portion. Note however that, in a case of using a surface coil, the temperature increase in a vicinity of a body surface is the major concern, so that there are cases in which it is useful to carry out the temperature measurement by using the above noted method in real time, and provide a feedback of the temperature increase information to the system.

In the present invention, the effectiveness of the temperature measurement can be improved by employing the temperature distribution measurement methods using various non-invasive imaging schemes which are attracting much attentions in recent years, in addition to the above noted temperature measurement methods.

For example, the system control can be realized according to the temperature data measured by utilizing temperature dependent parameters such as the transmission and reflection coefficients of ultrasonic waves, the absorption coefficient of X rays (which can be changed in relation to a change in a tissue density), the transmission coefficient of microwaves, etc. Here, it is required that the temperature measurement device is not influenced by the magnetic field very much and that the temperature measurement device does not adversely influence the MRI data acquisition. Consequently, it is necessary to incorporate an appropriate measure to that effect, such as a use of an ultrasonic wave source formed by non-magnetic materials.

Because of these limitations, It is more practical to use the temperature dependent parameters among the NMR parameters that can be acquired by the MRI, such as the density $\rho$, the longitudinal relaxation time T1, the transverse relaxation time T2, the self-diffusion coefficient D, and the chemical shift $\delta$. In particular, the acquisition of the parameters related to protons is advantageous from a viewpoint of the detection sensitivity, i.e., the measurement time.

However, in the existing reports, it has been pointed out that the temperature dependency of each temperature dependent parameter varies rather considerably depending on materials and tissues, so that it is ideal to use a parameter for which an influence of that kind is small so that a sufficient measurement precision can be secured and at the same time the shortening of the measurement time can be realized. Among those noted above, a method using the temperature dependency (−0.01 ppm/°C.) of the chemical shift of water proton is considered effective (see Japanese Patent Application Laid Open No. 5-253192 (1993)).

Figure 3:
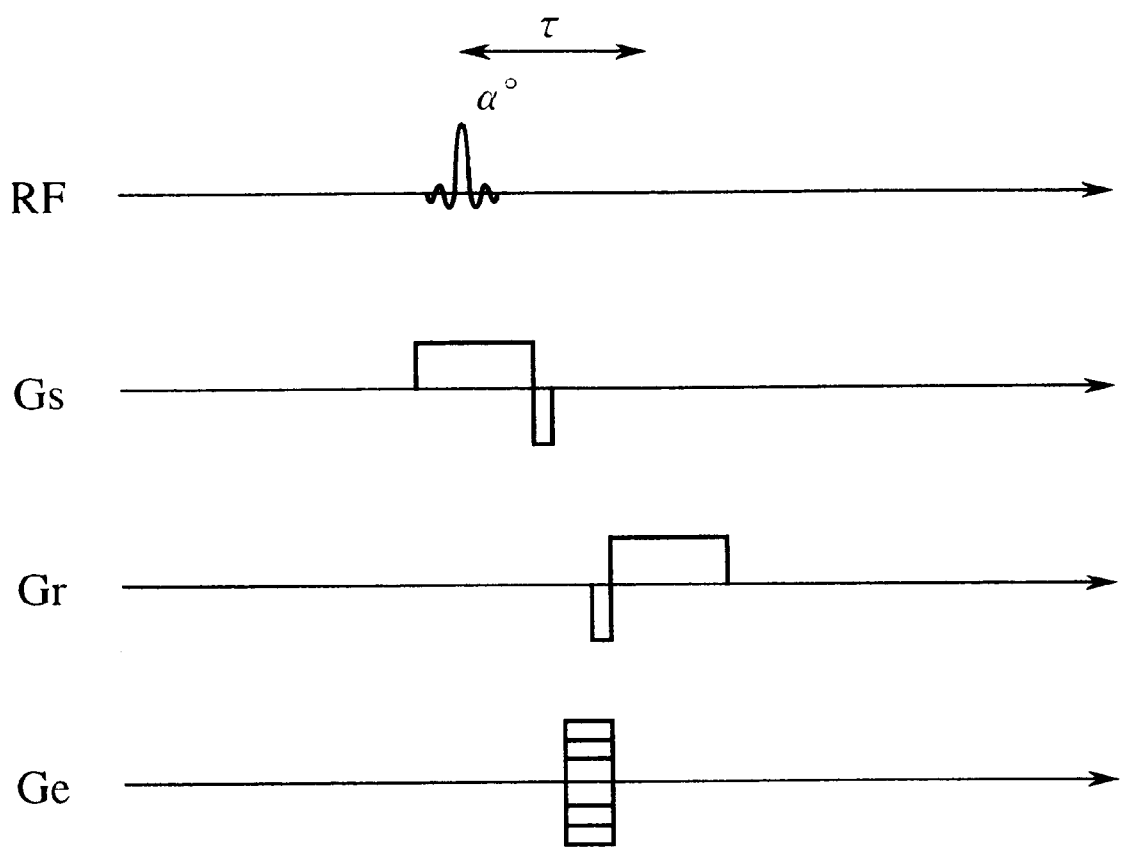
FIG. 3 is a sequence chart of one example of a field echo pulse sequence capable of obtaining a phase information associated with a temperature change.

In this method, a change of frequency due to the temperature change is encoded into a phase information possessed by the MR signals. Namely, as shown in FIG. 3, this method uses a pulse sequence which encodes a change of frequency due to the temperature change into a phase information of data by means of the echo time $\tau$. Note that, in FIG. 3, Gs indicates a slicing gradient magnetic field, Gr indicates a reading gradient magnetic field, and Ge indicates an encoding gradient magnetic field.

According to this method, a minute frequency change can be observed as an enlarged phase value change by adjusting the echo time $\tau$, so that the temperature measurement precision can be improved. In addition, it is possible to shorten the data acquisition time compared with a method for spatially observing spectrum.

By using the FE (Field Echo) pulse sequence shown in FIG. 3, a temperature change $\Delta T$ between two phase images $\theta$ acquired in a course of the temperature change can be calculated according to the following equation (1).

$$\Delta T(r)=T(r)\text{after}-T(r)\text{before}=\{\theta(r)\text{after}-\theta(r)\text{before}\}/\alpha\gamma\tau\beta_\theta \quad (1)$$

where r: a space vector,

α: a temperature dependency of water proton chemical shift,

γ: a nuclear gyromagnetic ratio,

τ: an echo time, and $\gamma_\theta$: a static magnetic field intensity.

Here, at a time of calculating a phase difference, it is advantageous from a viewpoint of a processing time to calculate a multiplication of a temperature to be calculated with the observed phase data (complext data), and then calculate a phase difference at that temperature, rather than to calculate phase values at different temperatures and then calculate their phase difference.

Note that the phase difference $\Delta\theta$ In this case can be expressed by the following equation (2).

$$\Delta\theta=\angle(e^{j\theta\text{after}}\times e^{-j\theta\text{before}}) \quad (2)$$

Figure 4:
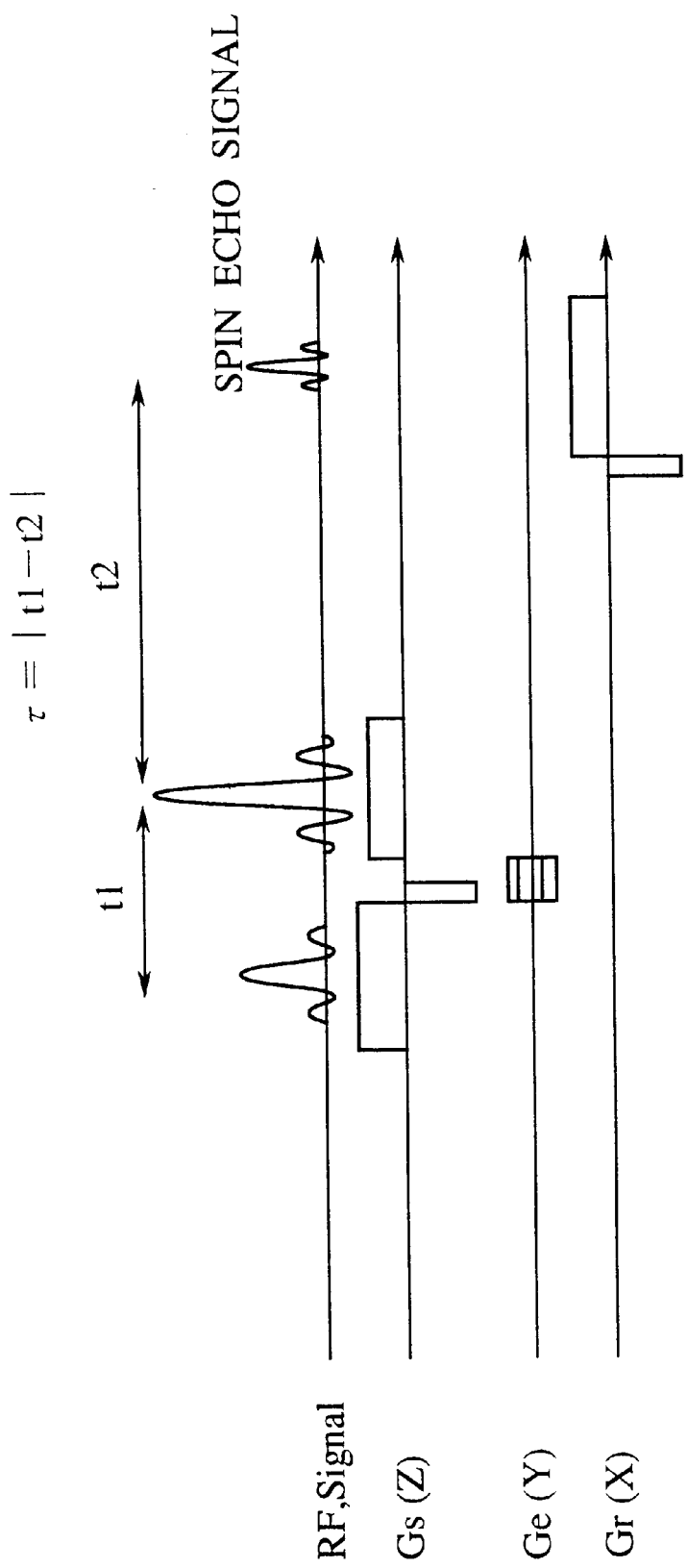
FIG. 4 is a sequence chart of one example of a spin echo pulse sequence capable of obtaining a phase information associated with a temperature change.

The available pulse sequences to acquire the phase information described above include the FE pulse sequence shown in FIG. 3 as well as the measurement pulse sequences based on various imaging schemes such as SE (Spin Echo) scheme shown in FIG. 4, EPI (Echo Planar Imaging) scheme, FSE (Fast Spin Echo) scheme, and GRASE (Gradient And Spin Echo) scheme.

Figure 5:
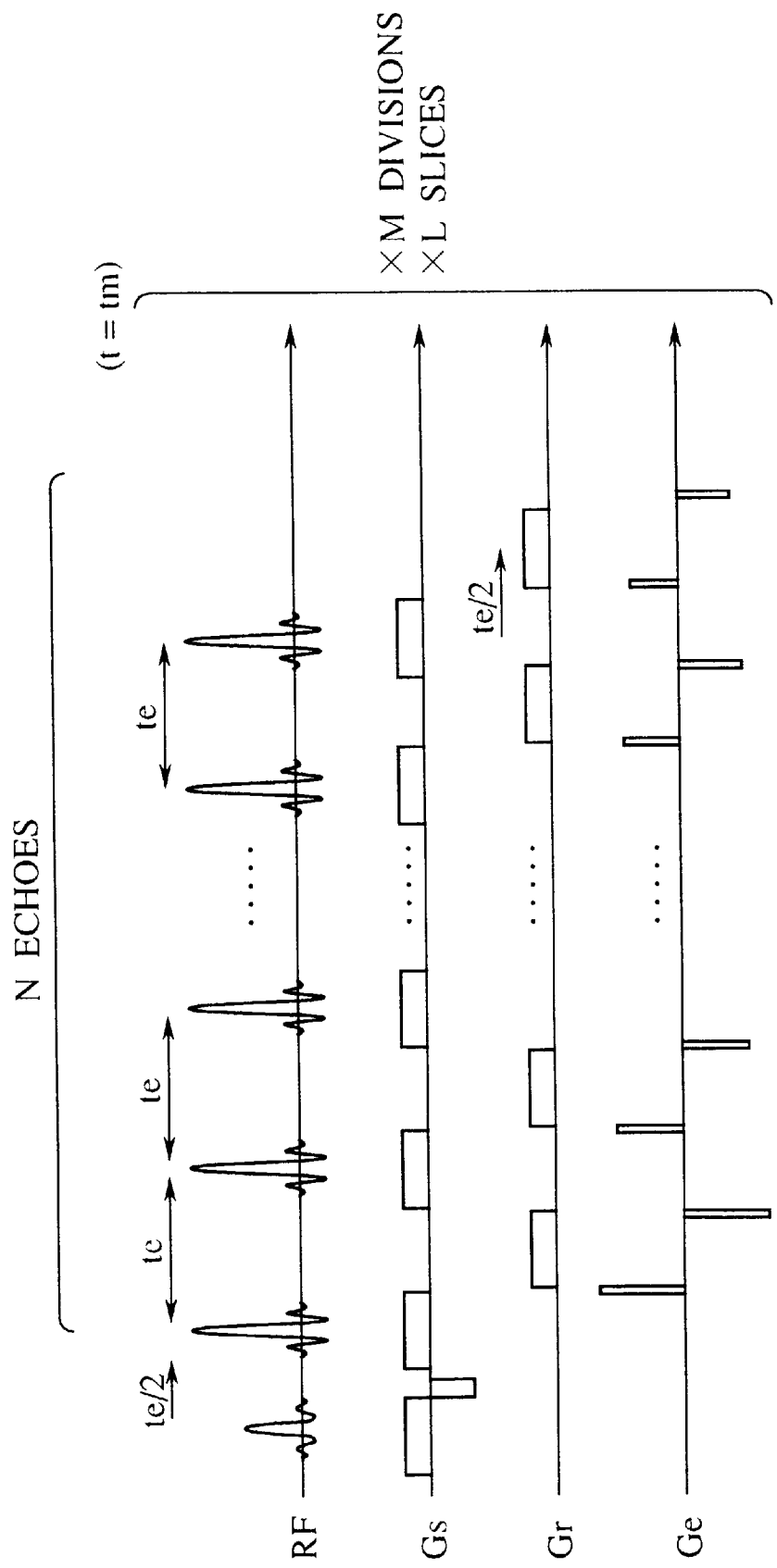
FIG. 5 is a sequence chart of one example of a high speed pulse sequence.

On the other hand, in recent years, a pulse sequence as shown in FIG. 5 which can acquire data at high speed by applying a plurality of RF magnetic fields including an RF selective excitation pulse (a first pulse in FIG. 5) and a plurality-of RF inversion pulses (second and subsequent pulses In FIG. 5) has been widely used for the purpose of shortening the data acquisition time. In such a pulse sequence, many RF magnetic fields (RF pulses) are applied in a short period of time, so that the problem of the temperature increase In an interior of a living body is more serious.

Figure 6:
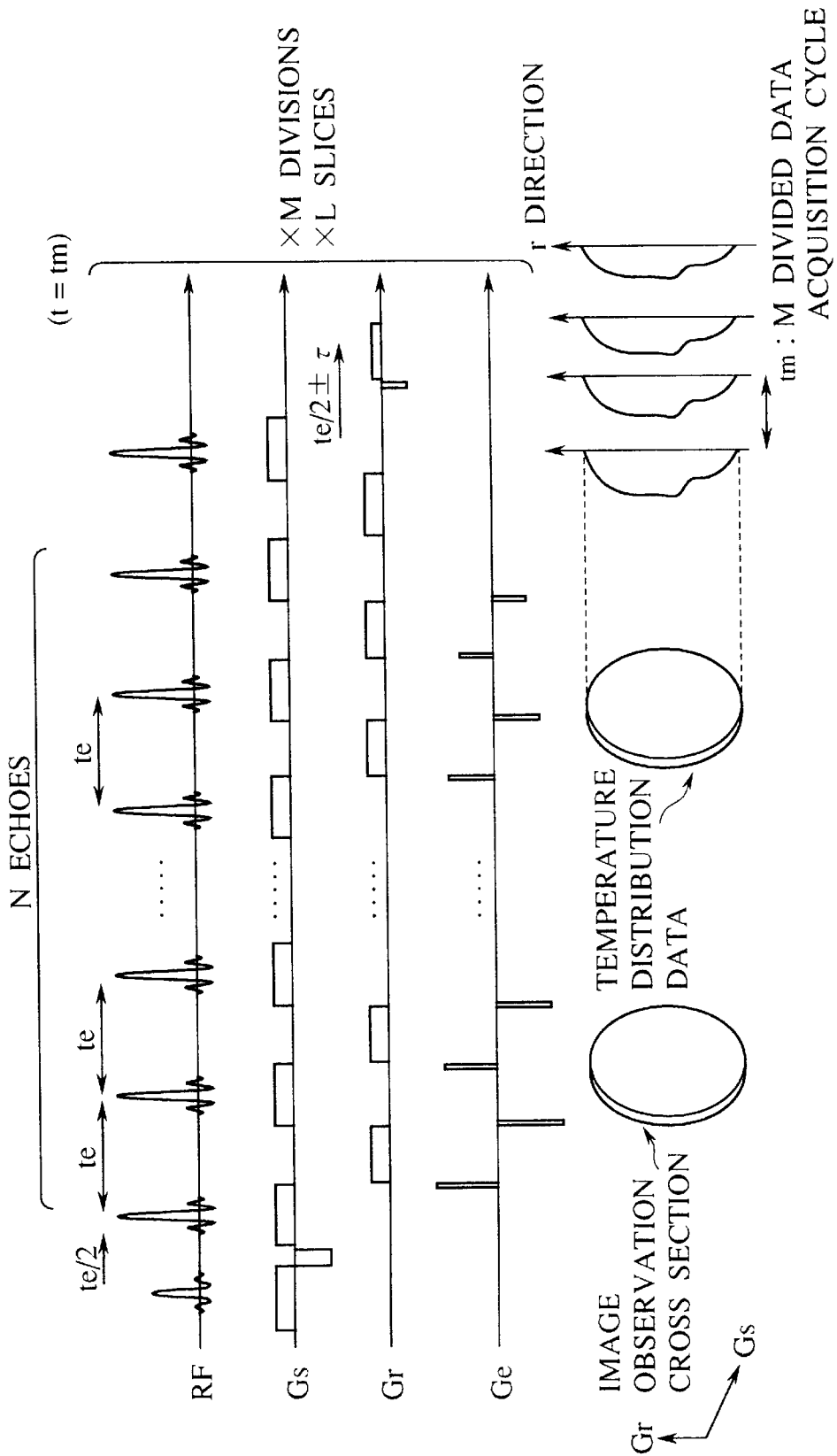
FIG. 6 is a sequence chart of one exemplary pulse sequence that can be used in the magnetic resonance imaging apparatus of FIG. 1.

Now, as shown in FIG. 6, by displacing either a signal observation start timing or an RF inversion pulse application timing for only a prescribed MR signal in the MR signal sequence constituting the normally desired image data in the pulse sequence of FIG. 5 (indicated by te/2±τ for Gr in FIG. 6), it is possible to acquire the above described phase information associated with the temperature change without adding any temperature measurement pulse sequence.

Here, however, in a case of the pulse sequence shown in FIG. 6, the phase information reflecting the temperature for each M divided scan (indicated by a time interval tm In the figure) can be observed at high speed (though slices may be different In some cases), but it is going to be a one dimensional projection of the temperature distribution on a cross section of the normally desired image data. Consequently, the measured data indicates an average value of the temperatures in such a region, and in a case the temperature distribution inside the measurement plane is in a steep shape, it is preferable to comprehend the temperature distribution by spatially localizing the measurement region.

Figure 7:
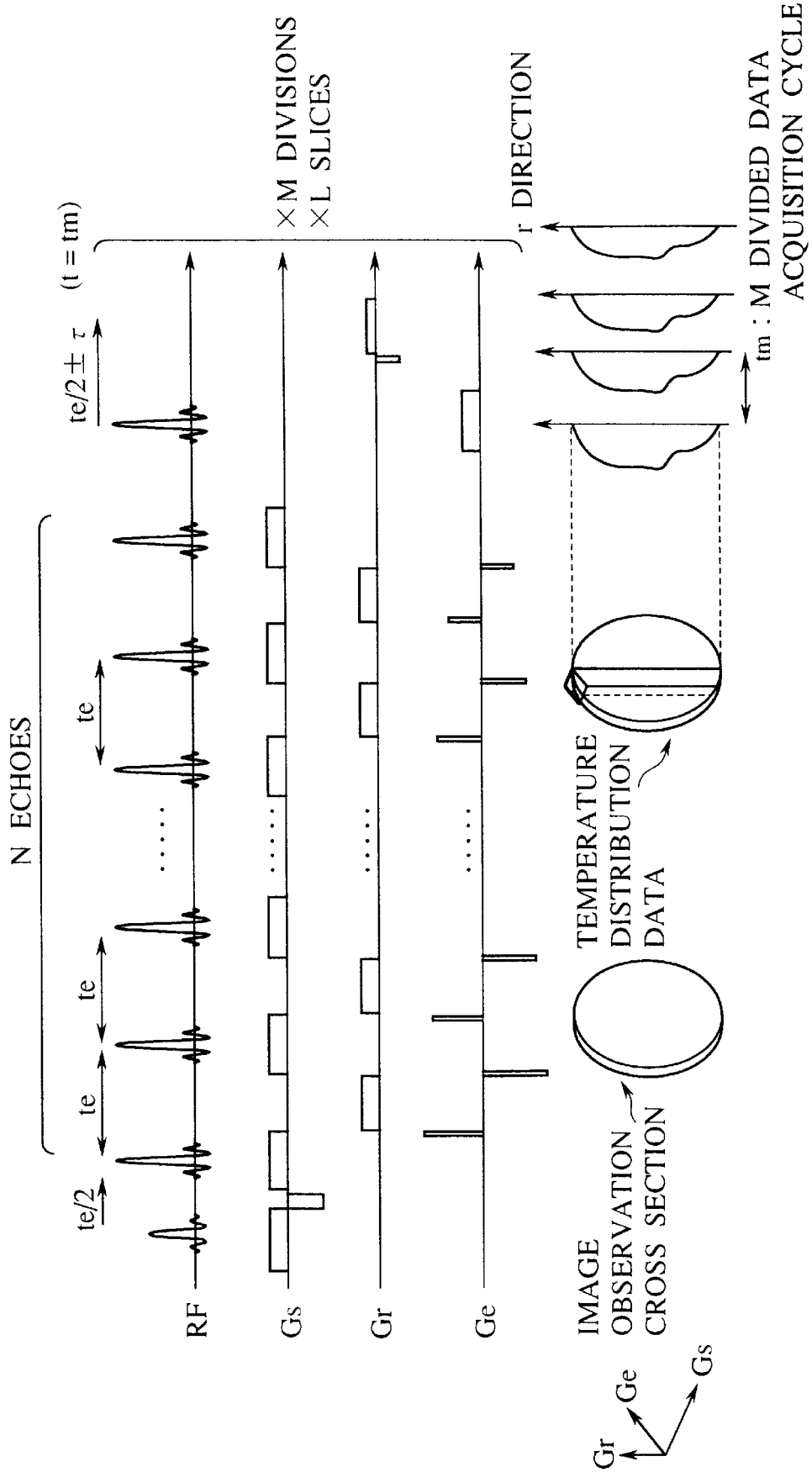
FIG. 7 Is a sequence chart of another exemplary pulse sequence that can be used in the magnetic resonance imaging apparatus of FIG. 1.

This can be realized by the pulse sequence as shown in FIG. 7, in which a direction of the gradient magnetic field to be applied simultaneously with the RF magnetic fields is selected to be a direction perpendicular to the target image observation cross section (a Ge direction in a case shown In FIG. 7), and the temperature distribution in one dimensional direction within a localized region In a column like shape.

Figure 8:
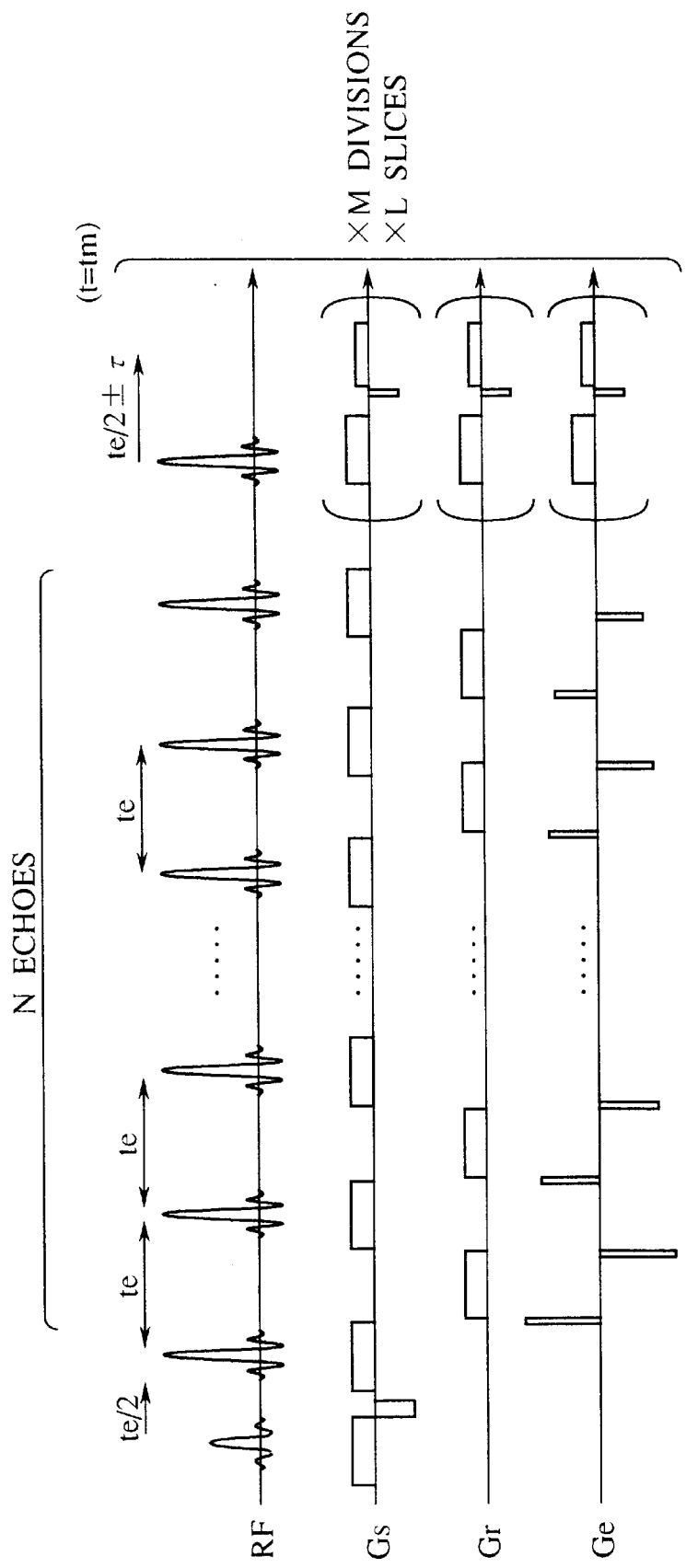
FIG. 8 is a sequence chart of another exemplary pulse sequence that can be used in the magnetic resonance imaging apparatus of FIG. 1.

Also, by adjusting the application direction of the gradient magnetic field and the offset frequency and the frequency bandwidth of the RF magnetic fields as indicated in FIG. 8, a size and a direction of a target from which the temperature data are to be acquired can be changed arbitrarily. Note however that, depending on an excitation direction, data to be imaged by the FSE pulse sequence may be affected, so that it is necessary to select these parameters by accounting for the parameters (such as TR/TE) of images to be acquired by the FSE scheme.

Figure 9:
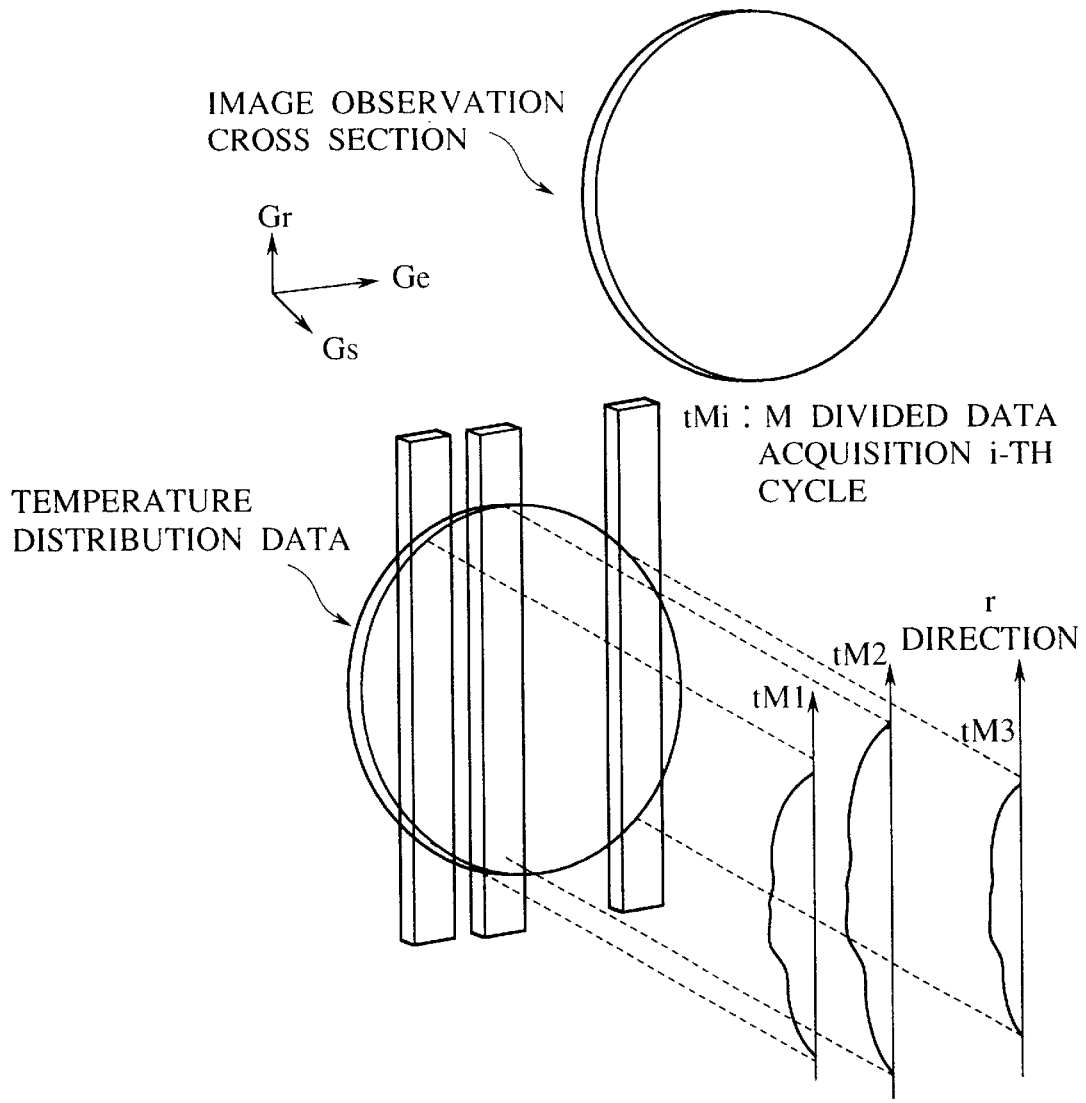
FIG. 9 is a diagram for explaining another exemplary pulse sequence that can be used in the magnetic resonance imaging apparatus of FIG. 1.

Within such a spatially localized region, the encoding of the temperature data can be made at each M divided scan, only for a necessary MR signal among N echoes, so that; by sequentially carrying out the above described adjustment of the gradient magnetic field application direction, the frequency offset of the RF magnetic field, etc., it is also possible to realize the acquisition of the spatial temperature distribution in time division as shown in FIG. 9. By acquiring such temperature distribution data, it becomes possible to comprehend the temperature distribution in further detail.

Also, in a case where the temperature increase is gradual compared with the measurement interval for obtaining the temperature data, it is also possible to acquire the two dimensional temperature distribution image by applying the phase encoding gradient magnetic field (for carrying out the phase encoding at each M divided scan, for example) in superposition to the reading gradient magnetic field.

As already mentioned above, it is also possible to acquire not just the spin echo signals but also the field echo signals as the signal sequences containing the temperature data.

In the method using the pulse sequence described above, the directly observed image data are phase values, so that there are cases in which the processing procedure for converting the phase values into the temperature data is added after the temperature measurement procedure. However, the temperature value and the phase value are in a proportional relationship as indicated by the equation (1), so that it is also possible to carry out the subsequent processing in terms of phases rather than temperatures.

The temperature data acquisition processing using any of the above described methods (temperature probe method, phase method, etc.) is repeatedly carried out, and the obtained temperature data are stored in the CPU/memory 20. Then, appropriate processing is applied to these temperature data by the temperature data processing unit 21, the display processing unit 22, the stopping processing unit 23, the re-activation processing unit 24, and the pulse sequence change processing unit 25.

Now, the outline of the processing carried out by the temperature data processing unit 21 will be described.

(1) Data storing:

The acquired data are stored into the CPU/memory 20 or media such as magnetic disks, for the sake of subsequent processing, while the stored data are utilized at a time of constructing a database to be used in statistically comprehending the temperature change due to individual differences. At this point, all measured data can be stored, but it is advantageous from a viewpoint of a storage capacity to extract the necessary data and store the extracted data alone.

(2) Calculation of a temperature difference from a reference value (a value of each parameter in a stationary state before data acquisition):

By calculating a temperature change from a reference state (stationary state), It is possible to comprehend a state change of an interior of a living body intuitively. Here, data measured by the temperature probe such as thermocouple is the absolute temperature in many cases, but the phase value measured by the above described phase method has a phase value due to inhomogeneity of the originally existing magnetic field superposed as a spatial offset distribution over a phase change due to the temperature change, so that the information reflecting the temperature of an interior of a living body cannot be comprehended unless a phase change from a certain reference state is calculated. To this end, the temperature difference can be calculated according to the equation (1) from a difference between phase distributions observed at arbitrary two time phases, but in a case of measuring the temperature difference, it is necessary to acquire the phase distribution In the stationary sate before the temperature increase is caused as a reference phase distribution θbefore appearing in the equation (1), and calculate the temperature change at each time phase.

The calculation result obtained by this processing is given to the display processing unit 22 and the stopping processing unit 23 to be described below.

(3) Calculation of a temperature difference from data measured at a previous measurement time:

By setting a reference point at a point immediately before the current data or several points before the current data and calculating differences from these data, when an abrupt temperature change occurs, it becomes possible to predict at that point that the subsequent temperature change is going to exceed the tolerable value. For this reason, It becomes Possible to apply the apparatus stopping measure before the temperature change is caused.

The calculation result obtained by this processing is given to the display processing unit 22 and the stopping processing unit 23 to be described below.

(4) Calculation of a change rate:

Similarly as in the above (3), by calculating a rate of change of the temperature data with respect to time, it becomes possible to apply the apparatus stopping measure when the change rate exceeds a threshold value.

The calculation result obtained by this processing is given to the display processing unit 22 and the stopping processing unit 23 to be described below.

(5) Calculation of a temperature time constant:

Similarly as in the above (3), the temperature time constant is also useful as an indicator in a case of stopping the apparatus, but this indicator is distinguished in that after the value is calculated, without stopping the apparatus immediately, approximately how much of the temperature increase is going to be caused can be predicted from the time constant, and that a level of safety can be predicted from a comparison (calculation of a difference or a ratio) with the time constant of the other body to be examined.

The calculation result obtained by this processing is given to the display processing unit 22 and the stopping processing unit 23 to be described below.

(6) Data smoothing:,

No matter which temperature measurement means is used, data have dispersion. In particular, the phase method can be affected by the signal noises rather easily so that there are cases in which an abrupt increase of the measurement data is an error caused by the noises. For this reason, it is useful to apply the smoothing to a plurality of measurement data. In this case, the phase fluctuation can be estimated according to the image S/N ratio, so that a number of points to be smoothed can be determined from the image S/N ratio.

Also, when only the spatially localized data are acquired, there are cases in which the temperature increase outside the tolerable range at a point which is not measured can be detected by applying a higher degree data interpolation to the acquired data.

The calculation result obtained by this processing is given to the display processing unit 22 and the stopping processing unit 23 to be described below.

(7) Curve fitting:

By carrying out a curve fitting processing to the continuously measured data and calculating parameter values, it becomes possible to comprehend the temperature increase more quantitatively. It also becomes easier to construct a database for temperature increase patterns. Also, at a time of display, there Is an advantage in that a prediction of the temperature increase can be made similarly as in the above (5), in addition to the effect of the smoothing similar to the above (6).

(8) Temperature change prediction:

In addition to a function to predict the temperature change by fitting a mathematical formula according to the temperature increase curve as in the above (5) and (7), it is possible to predict the temperature increase occurring within the measurement time from the time change rate of the temperature as in the above (4).

The information such as a time for reaching to the tolerable value which is obtained by this processing is given to the display processing unit 22, the stopping processing unit 23, and the pulse sequence change processing unit 25 to be described below.

(9) Temperature increase prediction using database:

At a time of predicting the temperature change in the above (8), a highly accurate prediction of a temperature increase can be made by utilizing the past temperature increase patterns stored as a database.

The result obtained by this processing is given to the display processing unit 22, the stopping processing unit 23, and the pulse sequence change processing unit 25 to be described below.

(10) Calculation of a maximum value:

In a case of measuring temperature data in a plurality of regions, by detecting a region which has the maximum value for the temperature or the temperature difference, it becomes possible to comprehend a portion which generates heat easily. According to this information, by carrying out the temperature measurements at its nearby regions in the subsequent measurements. It becomes possible to comprehend the temperature increase very minutely, and therefore a level of safety can be improved.

Also, by detecting and recording a time at which the temperature or the temperature difference becomes maximum for each body to be examined, it becomes possible to utilize this information as a reference at a time of the subsequent image data acquisition, regardless of whether a body to be examined is the same or not.

The calculation result obtained by this processing is given to the display processing unit 22, the stopping processing unit 23, and the pulse sequence change processing unit 25 to be described below.

(11) Set up of temperature data acquisition portions:

When a portion which has the maximum temperature (temperature change) is,detected as in the above (10), the pulse sequence is adjusted to set up excitation regions for the temperature measurements at its nearby regions. Also, by carrying out the set up processing for sequentially switching the temperature measurement regions, it becomes possible to evaluate the local temperature increase portion without overlooking.

(12) Set up of temperature data acquisition interval:

When the temperature change is gradual as a result of the processings of the above (2) to (4), it is not absolutely necessary to carry out the temperature measurements frequently. In such a case, a number of observed echoes can be increased in a case of the FSE by executing the temperature measurement and the temperature display processing to be described below at wider interval. Also at a time of storing, the storage capacity can be saved by storing only those data which will become necessary later. The pulse sequence can be modified flexibly by carrying out such a processing.

(13) Parameter conversion for measurement data:

The temperature dependent parameters of the MRI which can be directly measured are the signal strength, or the frequency value, or the phase. These parameters which are associated with the temperature change can be used directly as units of processing (signal strength units (which are usually normalized arbitrary units), frequency units, phase units) at the subsequent processing. However, at a time of displaying the result of the processing, a display in temperature units is more direct and intuitive so that a comprehension of a state of an interior of a living body becomes easier. For this reason, data are given to the display processing unit 22 after the parameter units are converted. On the other hand, in a case of giving data to the stopping processing unit 23, it is advantageous from a viewpoint of the processing time to continue the processing in units used by the measurements.

(14) Merging temperature data measured by a plurality of temperature measurement means:

As mentioned above, the temperature data measured according to the non-invasive temperature measurement method such as MRI are often given as changes from the stationary state (relative temperature). At a time of imaging, the temperature increase in an interior of a living body which requires the utmost attention is that of the brain which is a very heat sensitive organ (having a small heat resistance), but the temperature inside the brain is believed to be equal to the temperature of the rectum in the stationary state, and the correlation with the temperatures of the armpit, the forehead and the eardrum are also pointed out. Consequently, by measuring the armpit temperature (absolute temperature) under the stationary state by using the temperature probe such as thermocouple, setting this armpit temperature as a reference temperature, measuring the relative temperature of an interior of a living body such as the temperature inside the brain at a time of pulse sequence execution by using the non-invasive temperature measurement method, and adding this measured temperature to the reference temperature measured under the stationary state, it becomes possible to comprehend the absolute temperature approximately in addition to the relative temperature change.

By merging data measured by a plurality of temperature measurement means in this manner, it becomes possible to comprehend a state of an interior of a living body in further detail.

The calculation result obtained by this processing is given to the display processing unit 22, the stopping processing unit 23, and the pulse sequence change processing unit 25 to be described below.

(15) Processing for acquiring physiological function information of a body to be examined:

At a time of temperature measurement, by monitoring the physiological parameters which are considered necessary, such as an amount of sweating, a respiration rate, a pulse rate, a blood pressure, an electrocardiographic wave, a train wave, etc., it becomes possible to comprehend a state of a living body in further detail.

In a case of constantly measuring the physiological function parameters, by providing a function for judging a need for a switching of a display from that of the temperature increase to that of the physiological function parameters whenever necessary, it becomes possible to notify only necessary information to an operator.

By measuring these plurality of physiological function parameters and merging them with the temperature measurement data, it becomes possible to comprehend a state of an interior of a living body in further detail, and a level of safety can be improved.

The result obtained by this processing is given to the display processing unit 22 and the stopping processing unit 23 to be described below.

(16) Input/measurement of environmental data:

Even when the same RF magnetic field power (interval) is applied, depending on a difference in the environmental factors such as a room temperature, an amount of wilds, a humidity, etc., the temperature change in an interior of a living body can be largely different. In particular, in a case of carrying out the imaging using a surface coil, the body temperature increase can be largely different depending on a presence or absence of a cooling wind. Such environmental data are measured at a time of the temperature measurement, merged with the temperature measurement data and given to the display processing unit 22 to be described below, or given to the apparatus stopping processing and used as an indicator for the apparatus stopping.

The temperature data such as the temperature or the temperature change calculated by the temperature data processing unit 21 as described above are entered into the display processing unit 22, processed therein and outputted (displayed) on a terminal (display screen) In various formats. By means of this display, it is possible to notify a state of the temperature increase in a body to be examined to an operator.

It is preferable to display the temperature data processing result within a sub-window which occupies a part of the display screen as shown in FIG. 10A, for the convenience of the other processing operations. In a case where the temperature data are obtained as time series data, the displayed data are regularly updated. As a display format within this sub-window, any of the numerical display formats as illustrated In FIGS. 10B, 10C, 10D, 10E and 10F can be used.

FIG. 10B shows a format for displaying the temperature data which is changing in time by overwriting old data by new data.

FIG. 10D shows a format for displaying records of the temperature data for each time t, while simultaneously displaying an indication of a measurement position X.

FIG. 10E shows a format suitable in a case where the temperature data for a plurality of regions are calculated, in which a part or a whole of these temperature data are displayed along with the respective measurement positions X.

FIG. 10F shows a format suitable in a case where a time span is too long or a number of measurement regions are too many for easy comprehension, in which the desired temperature data are displayed either by entering a desired position or time, or by scrolling the window display by using a scroll bar, by means of a mouse or a keyboard.

Figure 11A:
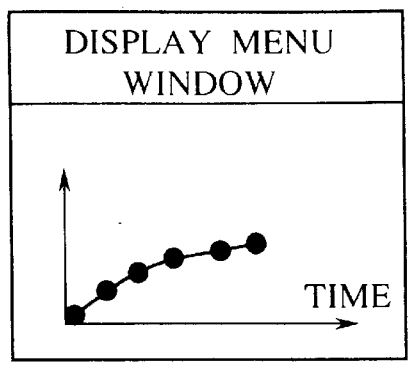
FIGS. 11A to 11G are illustrations of some other exemplary temperature data display formats that can be used in the magnetic resonance imaging apparatus of FIG. 1.

FIG. 11A shows a format for displaying the time series temperature data in a form of a graph. Any desired type of graph may be used in this display format.

Figure 11B:
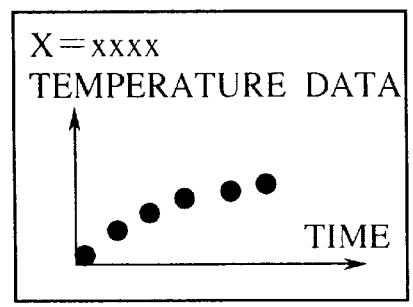

FIG. 11B shows a display format in which the temperature data measured at each time is sequentially plotted. In this case, a total measurement time can be automatically set up to the horizontal axis according to the executed pulse sequence in advance so that an entire time span can be displayed by normalizing it, or data in a sequential or arbitrary time span can be displayed.

Figure 11E:
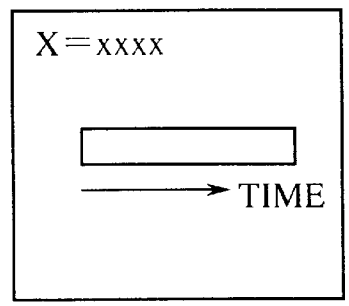
Figure 11C:
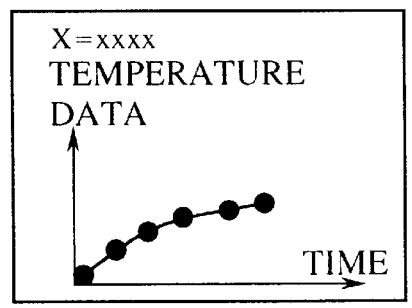

FIG. 11C shows a display format in which the measurement data points are Joined by line segments or curves.

Figure 11F:
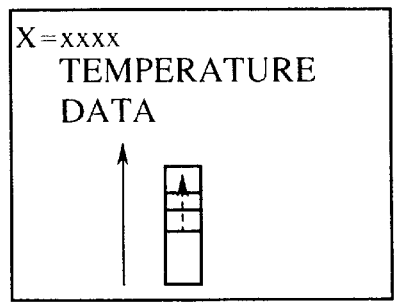
Figure 11D:
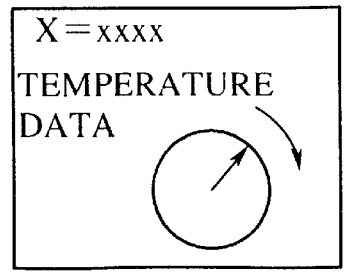

FIG. 11D shows a format for displaying the temperature data in a form of circular graph.

FIG. 11E shows a format for displaying the time change of the temperature data at a certain position X in terms of image Intensity levels. For example, a lower temperature state is indicated by a lower image intensity while a higher temperature state is indicated by a higher image intensity.

FIG. 11F shows a format for displaying the temperature data at a certain position X in a form of bar graph, where a taller bar height indicates a higher temperature state.

Figure 11G:
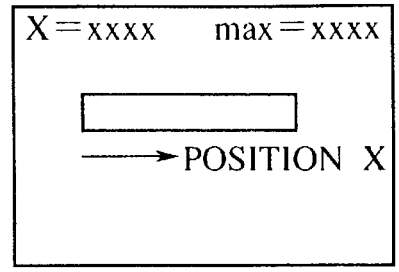

FIG. 11G shows a display format suitable for a case of having a plurality of temperature data measurement regions (or a case of having a wide ranging temperature data measurement region), in which the position X is indicated by a horizontal axis while the temperature at each position is indicated by the image intensity level. By using the display of this FIG. 11G, it becomes easier to comprehend a position at which the temperature is increasing, and by indicating additional information such as a corresponding body portion name and a maximum temperature, it becomes possible to comprehend the temperature state of an interior of a body to be examined in detail.

Figure 12:
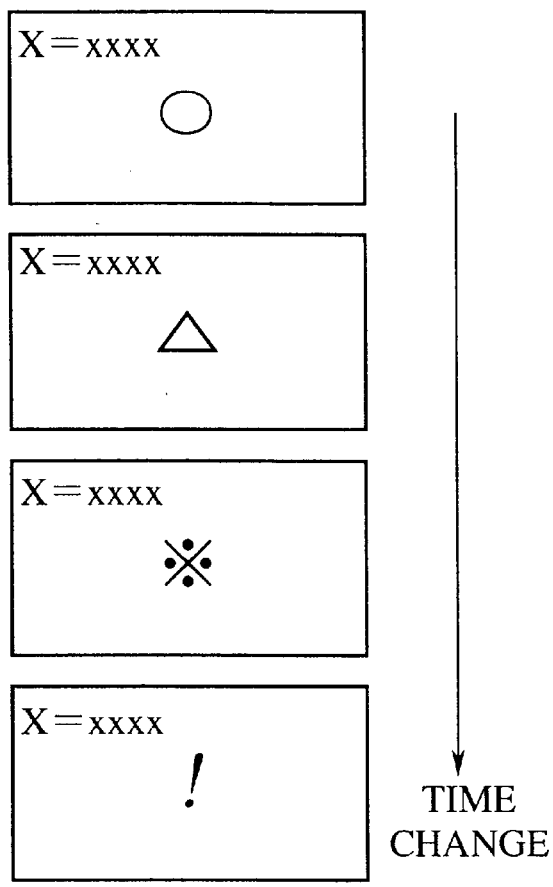
FIG. 12 is an illustration of another exemplary temperature data display format that can be used in the magnetic resonance imaging apparatus of FIG. 1.

It is also possible to display the temperature increase in a visually appealing way by variously changing figures according to the temperature values as shown in FIG. 12. Also, instead of the figures, it is also possible to indicate the temperature state change by means of colors, a change of brightness, lighting/flashing, sounds, vibrations, etc.

For the display items, apart from the temperature data, it is also possible to display a time, coordinates of a point when the spatial information is available, or their combination. Also, when the measurement extends over a long time, it becomes necessary for the display to be capable of being scrolled or overwritten, and as the support functions of the sub-window, it is preferable to provide a scroll bar and a coordinates input window, as already indicated in FIG. 10F.

It is also preferable for the display as described above to be capable of being displayed in various modes that can be appropriately switched, such as a display mode and a non-dIsplay mode that can be selected by an operator whenever an operator finds the need, a mode for displaying the temperature data only when the temperature increase is recognized, etc.

Figure 13:
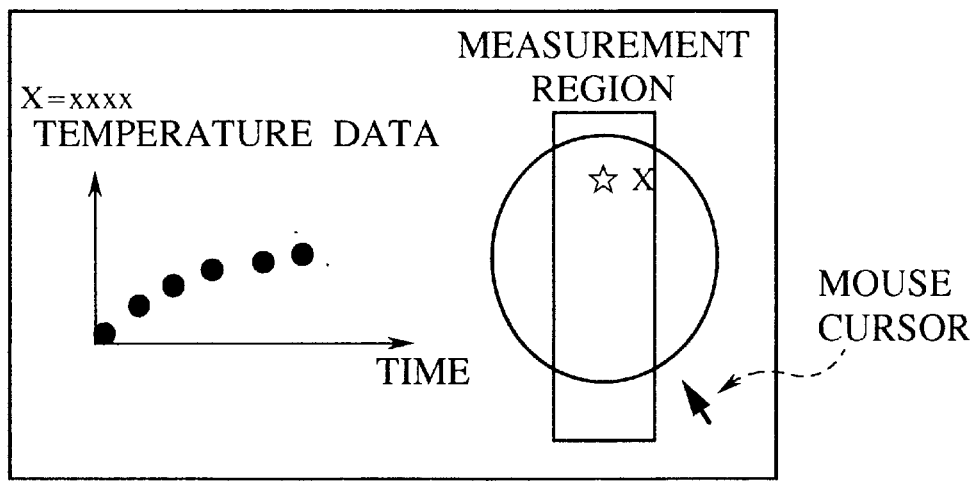
FIG. 13 is an illustration of another exemplary temperature data display format that can be used in the magnetic resonance imaging apparatus of FIG. 1.

In a case of indicating the spatial temperature data, as shown in FIG. 13, it is effective to superpose positions of the measured temperature data over a figure representing a body to be examined, or an image obtained by actually imaging a body to be examined, in order to comprehend a spatial state of the temperature increase. It is preferable to explicitly indicate a body portion for which the temperature data are displayed according to a number of dimensions of the acquired temperature data, as shown in FIG. 13.

On the other hand, it is useful to make it possible to freely select a body portion for which the temperature data are to be displayed by using a mouse, etc., or to have a processing for changing a displayed body portion in time division, in order to prevent an overlooking of the temperature increased body portion when a local temperature increase is predicted. In addition, it is preferable to use the pulse sequence which can be modified in such a manner that the temperature of a body portion specified by a mouse will be measured.

In a case of the two dimensional temperature measurement data, It is possible to display the temperature data of each body portion on a plane, but in this case, it is also preferable to be capable of displaying the temperature data of an arbitrary body portion in any of the formats described above. When it is possible to select any of the various display formats as shown in FIGS. 11A to 11G, 12 and 13 in a form of a menu of the window, it becomes possible to set up data desired to be comprehended by an operator according to an operator, so that the apparatus can be operated at an improved reliability.

It is very useful from viewpoints of the apparatus stopping to be described below and the confirmation of the safety of a body to be examined, to display a numerical value (FIG. 14A) or a marking such as a line (FIGS. 14B, 14C, 14C, 14D and 14F) indicating a threshold value or a specified In order to comprehend a rate or a tolerable value of the temperature increase in an interior of a body to be examined. For a threshold value, an absolute temperature (such as a temperature that can be tolerated by the measured body portion: 42 to 44° C. for skin, 42 to 43° C. for brain, etc.) or a temperature change from the stationary state (4 to 6° C., for example) can be specified. Also, these indications may be given with some range to account for the individual differences and the measurement errors (FIG. 14E). In addition, it is also effective to display a difference from such an indication (threshold value), from a viewpoint of reducing an operation error by an operator in relation to the apparatus stopping.

Here, the displayed quantity may not necessarily be given in temperature units, and it is also advantageous from a viewpoint of the, processing time to directly display the temperature parameter (such as phase value) used in measuring the temperature. Also, by using the temperature parameters (such as signal strength and phase value) for an internal processing and converting a display scale of the threshold value, etc., Into these units, it is possible to omit unnecessary calculations. These processings are already carried out by the temperature data processing unit 21, and the display is made by recognizing flags, etc., which Indicate the units in which the temperature data are processed.

Figure 15A:
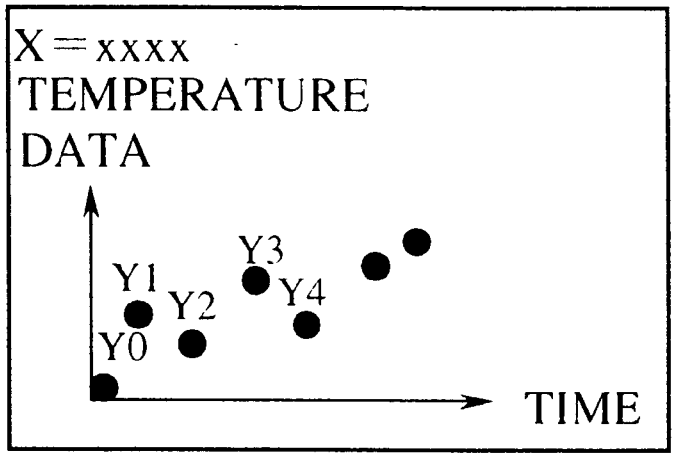
FIGS. 15A and 15B are illustrations of some other exemplary temperature data display formats that can be used in the magnetic resonance imaging apparatus of FIG. 1.
Figure 15B:
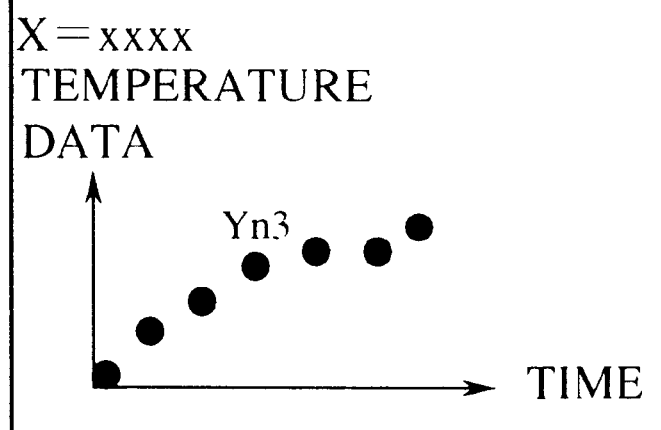

As already described for the temperature data processing unit 21, there are cases in which sufficient signals cannot be obtained depending on the temperature measurement regions, and it is preferable to display all the measurement data for several points in past, rather than just displaying a current measurement value (actual measurement value) alone, in order to account for an influence of erroneous measurements due to noises. For example, for the actual measurement data for past four points (Y0, Y1, Y2, Y3) as shown in FIG. 15A, a mean value Yn3 can be calculated:and displayed as shown in FIG. 15B.

Also, by sequentially re-processing the past data by using newly measured data (calculating a mean value by using data on several points around a point of interest) as the measurement progresses and updating the display, it is possible to improve the measurement reliability.

It is preferable to carry out this processing according to the predicted image S/N ratio, automatically at the temperature data processing unit 21. However, there can be a case In which the smoothing is not carried out at the temperature data processing unit 21 so that how poor the S/N ratio is can be ascertained only after the display is made, and in such a case, it is preferable to provide the smoothing function in the display processing unit 22 so that the smoothing processing can be turned ON/OFF while watching the display.

Next, the stopping processing unit 23 will be described.

By the temperature data measurement and the output (display) of its result, it becomes possible for an operator to comprehend a state of a body to be examined, and when the temperature increase due to the RF magnetic field is recognized, or when it can be predicted from a time series change of the temperature increase that the temperature increase is going to exceed the tolerable value by the further execution of the pulse sequence, it is possible to apply the measure to stop the execution of the pulse sequence or to interrupt the apparatus, so that it is possible to secure the safety of a body to be examined.

As the criteria for Judging the interruption of The apparatus, the following criteria can be used:

(a) When the parameter value calculated by any of the processings (2) to (10) and (13) of the temperature data processing unit 21 exceeds a prescribed reference value;

(b) For the parameter values calculated by any of the processings (2) to (10) and (13) of the temperature data processing unit 21, when a difference between the values calculated within a certain period of time exceeds a prescribed reference value;

(c) For the parameter values calculated by any of the processings (2) to (10) and (13) of the temperature data processing unit 21, when a ratio of the values calculated within a certain period of time exceeds a prescribed reference value:

(d) When a ratio of the parameter value calculated by any of the processings (2) to (10) and (13) of the temperature data processing unit 21 and a prescribed reference value exceeds another prescribed reference value; and (e) When the parameter value and the measured temperature data measured or calculated by any of the processings (14) to (16) of the temperature data processing unit 21 exceed certain reference values.

When any of these Judgement criteria is satisfied, the CPU/memory 20 notifies the fact that the temperature of an interior of a living body exceeded a reference value to an operator through an output device such as a display. When an occurrence of such a state is comprehended, an operator enters an input on an Input terminal or a mouse Input on a window level to generate a pulse sequence stop signal. This signal is then outputted to the sequence controller 19, and the sequence controller 19 is stopped.

Also, in order to make sure to stop the application of the RF magnetic fields on a living body, the output of the transmission amp (RF amp) 17 is blocked. Else, in order to suppress the output, a signal is sent to a control circuit for operating a protection circuit of the transmission amp 17, etc.

These mechanisms for stopping the sequence controller 19 and the transmission amp 17 may be operated independently, but a level of safety of a body to be examined can be improved by operating them simultaneously.

There are cases in which it is effective to carry out these stopping operations optionally at optional timings according to a Judgement of an operator watching the display of the temperature data. Namely, there are individual differences for the temperature sensitivity (that is, the temperature may be found intolerable even if it is below the tolerable value), so that the stopping timing can be Judged according to the communication with a body to be examined, in addition to the displayed temperature data.

On the contrary, there can be a body portion in which the tissue damage is caused despite of the fact that a body to be examined is not aware of the heat generation (a body to be examined judges himself that the application of the RF magnetic fields is possible) according to the communication with a body to be examined, so that it is often effective from a viewpoint of safety to control these stop signals numerically by the control/processing CPU in accordance with the above described judgement criteria.

When it is judged that the apparatus should be stopped, the CPU/memory 20 sends the apparatus stop signals to the sequence controller 19 and/or the transmission amp 17 similarly as described above, to stop a part or a whole of the apparatus. When the stopping of the apparatus is commanded and the apparatus is stopped, it is preferable to display the fact that the apparatus has stopped on a system display. In this case, it is also preferable to display the judgement criteria which caused the stopping of the apparatus, and the devices (sequence controller, transmission amp) to which the apparatus stop commands are issued.

Also, when the stop signals are issued, the stopping processing unit 23 issues a command as to whether or not to store the signal sequences acquired so far. This is done so that when a state in which the execution of the pulse sequence is possible is recovered, only the remaining data sequences are acquired instead of executing the entire pulse sequence once again, so as to shorten the measurement time.

This is a function which becomes necessary when the remaining data acquisition is to be carried out In division as it is predicted that the temperature increase occurs again when the entire pulse sequence is executed. However, there can be a case in which the data sequences acquired before and after the pulse sequence interruption cannot be handled uniformly because of the influence of the acquisition parameters, and in such a case, there is a need to re-construct the pulse sequence which realizes the RF magnetic field condition (temperature increase condition) for guaranteeing the safety of a body to be examined, as will be described below.

For the processings described above, the same CPU as used for the acquisition and the processing of the desired image data is usually used, but when the data processing CPU has a performance level by which the processing of the signal sequences containing the temperature data and the image data processing cannot be carried out simultaneously, in order to display the temperature data at high speed, only prescribed MR signal sequences are extracted and the necessary processing is subsequently carried out for these signal sequences alone. In this case, the other image data are saved in a buffer, and the necessary processing is going to be applied after the acquisition of all image data. Else, it is also possible to provide a dedicated CPU/data processor for carrying out the temperature processing in real time.

When the temperature increase in an interior of a body to be examined exceeded a specified value and the sequence controller and the RF amp are stopped, it should be avoided to re-start the subsequent pulse sequence immediately. This is because the temperature increase is easily caused while the temperature of an interior of a body to be examined has not returned to the stationary state.

In order to avoid such a situation, before the pulse sequence for observing the desired MR signal sequences is executed, the pulse sequence for observing the temperature data alone is executed, and the re-activation processing unit 24 judges whether the temperature is in a state for allowing the re-execution of the pulse sequence or not.

This judgement Is made by executing the temperature measurement pulse sequence at an arbitrary time or at each constant period, in order to omit a waste of time until the re-execution. In this case, in order to judge that it returned to the stationary temperature state the temperature data in the stationary state is acquired in advance, and the temperature recovery process after the apparatus stopping is compared with this data.

It is also possible to predict a timing at which the re-execution of the pulse sequence becomes possible as the temperature recovers the stationary state, by acquiring the time series temperature data for a certain period of time as described above, and in such a case, there is no need to carry out the subsequent acquisition of the temperature data frequently, and it suffices to carry out the subsequent acquisition of the temperature data only when the need arises.

When the re-activation processing unit 24 judges that the temperature of an interior of a living body is in the stationary state or has recovered to a specified value according to the acquired temperature data, the pulse sequence re-execution signals are sent from the CPU/memory 20 to the sequence controller 19 and the transmission amp 17, and thereafter the pulse sequence is re-executed without wasting any time.

Here, when the same pulse sequence as that which caused the temperature increase resulting in the stopping of the apparatus is re-executed under the same condition. it is expected that the temperature increase will be caused again provided that a body to be examined is in the same state as before. In such a case, It is possible to apply the measure to cool a body to be examined, but it is preferable to optimize the pulse sequence according to the measured temperature data.

This processing is carried out by the pulse sequence change processing unit 25, by changing parameters of the pulse sequence to be executed next time according to the reference values and the desired data measurement time regarding the parameters which exceeded the apparatus stopping judgement criteria.

As for the manner of changing the pulse sequence, the first things to do is to suppress the pulse power and to increase the pulse application time span. It is also possible to reduce a number of RF pulses to be applied, or to widen the RF pulse application interval. At this point, there are cases in which the imaging parameters are affected, so that there is a need to change the pulse sequence by accounting for the influence of these changes on the images.

In making these changes, the parameters of a new pulse sequence are set up according to prescribed calculation rules by accounting for the measurement value, the reference value (tolerable value), a time to reach to the reference value, and the temperature change rate. For example, when the temperature change rate is constant, according to a ratio a of the image acquisition time and a time for the temperature measurement value to reach to the reference value, the input power is set to be not greater than $1/\alpha$. Similarly, it is also possible to set the time interval a times longer, or to set a time between divisions $\alpha$ times longer in a case of carrying out the FSE in M divisions.

In a case of changing the RF pulse power, etc., automatically, it is necessary that an operator enters the current RF pulse input power (input voltage), application interval, application period, and pulse waveform, or these factors are measured automatically, or else these factors are read out from a file storing these factors in advance.

On the other hand, in a case of acquiring the image data by using the surface coil, it is possible to avoid the local temperature increase by changing a distance between the surface coil and a body to be examined at a time of executing the pulse sequence next time, instead of changing the pulse sequence. For example, when the temperature change rate is constant, according to a ratio $\alpha$ of the image acquisition time and a time for the temperature measurement value to reach to the reference value, by changing a distance between the surface coil and a body to be examined $\alpha^{1/2}$ times greater, it is possible to acquire the desired image data while suppressing the temperature increase.

As described, according to the present invention, the temperature increase in an interior of a body to be examined due to an application of the RF magnetic fields is measured and displayed, so that it becomes possible to notify a state of a body to be examined to an operator, and it becomes possible to secure the safety of a body to be examined.

It is to be noted that, besides those already mentioned above, many modifications and variations of the above embodiments may be made without departing from the novel and advantageous features of the present invention. Accordingly, all such modifications and variations are intended to be included within the scope of the appended claims.

What is claimed is:

1. A magnetic resonance imaging apparatus, comprising:

imaging means for observing a magnetic resonance signal sequence by applying a slicing gradient magnetic field in a prescribed direction to a body to be examined placed in a static magnetic field, while applying radio frequency magnetic fields including a radio frequency selective excitation pulse and a plurality of radio frequency inversion pulses in prescribed intervals to the body to be examined according to a prescribed pulse sequence for producing the magnetic resonance signal sequence formed by a plurality of magnetic resonance signals; and control means for controlling the imaging means to acquire image data and a phase information associated with a temperature change in an interior of the body to be examined, by displacing a timing in the pulse sequence for a prescribed magnetic resonance signal among said plurality of magnetic resonance signals constituting the magnetic resonance signal sequence, from a normal timing assigned to the prescribed magnetic resonance signal for acquiring only the image data.

2. The apparatus of claim 1, wherein the control means controls the imaging means to acquire the phase information associated with a temperature change the interior of the body to be examined, by displacing an observation start timing for the prescribed magnetic resonance signal in the magnetic resonance signal sequence from the normal timing for acquiring image data.

3. The apparatus of claim 1, wherein the control means controls the imaging means to acquire the phase information associated with a temperature change in the interior of the body to be examined, by displacing a radio frequency inversion pulse application timing for the prescribed magnetic resonance signal in the magnetic resonance signal sequence from the normal timing for acquiring image data.

4. The apparatus of claim 1, wherein the control means also controls the imaging means to use a direction to apply the slicing gradient magnetic field for the prescribed magnetic resonance signal which is different from the prescribed direction.

5. The apparatus of claim 1, wherein the control means also controls the imaging means to use a direction to apply the slicing gradient magnetic field for the prescribed magnetic resonance signal which is perpendicular to a cross section for observing the magnetic resonance signal sequence.

6. The apparatus of claim 1, wherein the control means also controls the imaging means to observe the magnetic resonance signal sequence while applying a gradient magnetic field in an arbitrary direction after the slicing gradient magnetic field for the prescribed magnetic resonance signal is applied.

7. The apparatus of claim 1, wherein the control means also controls the imaging means to change any one of a direction to apply the slicing gradient magnetic field for the prescribed magnetic resonance signal, an offset frequency of the radio frequency magnetic fields, and a frequency bandwidth of the radio frequency magnetic fields, so as to set up a size and a direction of an observation target.

8. The apparatus of claim 1, wherein the control means also controls the imaging means to apply a phase encoding gradient magnetic field In superposition to a reading gradient magnetic field for the prescribed magnetic resonance signal, so as to acquire two dimensional temperature distribution.

9. The apparatus of claim 1, further comprising means for obtaining temperature data from the phase information.

10. The apparatus of claim 9, further comprising means for storing sequentially obtained temperature data.

11. The apparatus of claim 10, further comprising means for obtaining a temperature of the interior of the body to be examined, according to the sequentially obtained temperature data and a reference value indicating a stationary state.

12. The apparatus of claim 10, further comprising means for predicting a case in which a temperature of the interior of the body to be examined exceeds a tolerable value, according to a change rate of the sequentially obtained temperature data.

13. The apparatus of claim 12, further comprising means for interrupting the pulse sequence when the temperature of the interior of the body to be examined exceeds or is predicted to exceed the tolerable value.

14. The apparatus of claim 13, further comprising means for storing the magnetic resonance signal sequence observed before the pulse sequence is interrupted.

15. The apparatus of claim 14, wherein the control means controls the imaging means to re-execute the pulse sequence from a point where the pulse sequence is interrupted, when the temperature of the interior of the body to be examined returns to a value not exceeding the tolerable value.

16. The apparatus of claim 15, wherein the control means controls the imaging means to use different conditions on an application of the radio frequency magnetic fields before the pulse sequence is interrupted and after the pulse sequence is re-executed.

17. The apparatus of claim 12, further comprising means for predicting a future temperature increase by calculating a temperature time constant from the change rate.

18. The apparatus of claim 10, further comprising means for smoothing the sequentially obtained temperature data.

19. The apparatus of claim 10, further comprising means for interpolating the sequentially obtained temperature data.

20. The apparatus of claim 10, further comprising means for carrying out a curve fitting to the sequentially obtained temperature data.

21. The apparatus or claim 20, further comprising means for storing a temperature change pattern obtained by the curve fitting.

22. The apparatus of claim 21, further comprising means for predicting a future temperature increase according to the temperature change pattern.

23. The apparatus of claim 10, further comprising means for identifying a body portion at which the temperature of an interior of the body to be examined increases by detecting a region having a maximum value for the sequentially obtained temperature data.

24. The apparatus of claim 23, further comprising means for detecting and recording a time required for the sequentially obtained temperature data to reach to the maximum value.

25. The apparatus of claim 23, wherein the control means controls the imaging means to set up excitation regions for temperature measurement in a vicinity of said region having the maximum value for the sequentially obtained temperature data.

26. The apparatus of claim 10, further comprising display means for displaying the sequentially obtained temperature data in a prescribed display region.

27. The apparatus of claim 26, wherein the display means also displays one of a tolerable value and a threshold value in the prescribed display region.

28. The apparatus of claim 26, wherein the display means also displays a change rate of the sequentially obtained temperature data in the prescribed display region.

29. The apparatus of claim 9, wherein the temperature data indicates one of a temperature change in the interior of the body to be examined and a temperature of the interior of the body to be examined.

30. A method of magnetic resonance imaging comprising the steps of:

observing a magnetic resonance signal sequence by applying a slicing gradient magnetic field in a prescribed direction to a body to be examined placed in a static magnetic field, while applying radio frequency magnetic fields including a radio frequency selective excitation pulse and a plurality of radio frequency inversion pulses in prescribed intervals to the body to be examined according to a prescribed pulse sequence for producing the magnetic resonance sequence formed by a plurality of magnetic resonance signals; and controlling the imaging step to acquire image data an a phase information associated with a temperature change in an interior of the body to be examined, by displacing a timing in the pulse sequence for a prescribed magnetic resonance signal among said plurality of magnetic resonance signals constituting the magnetic resonance signal sequence, from a normal timing assigned to the prescribed magnetic resonance signal for acquiring only the image data.

* * * * *